(12) United States Patent
Ogushi et al.

(10) Patent No.: US 6,732,734 B2
(45) Date of Patent: May 11, 2004

(54) PILOT BALLOON FOR BALLOON CATHETERS

(75) Inventors: Masayasu Ogushi, Tsukuba (JP); Kyoichiro Shibatani, Tokyo (JP); Toshihide Nakashima, Kurashiki (JP); Motohiro Fukuda, Tsukuba (JP); Toshiyuki Zento, Tsukuba (JP); Yasuzo Kirita, Osaka (JP); Yukihiro Fujieda, Kurashiki (JP); Chuck Bates, South Glens Falls, NY (US)

(73) Assignee: Kuraray Co., Ltd., Kurashiki (JP)

( * ) Notice: Subject to any disclaimer, the term of this patent is extended or adjusted under 35 U.S.C. 154(b) by 0 days.

(21) Appl. No.: 09/842,794

(22) Filed: Apr. 27, 2001

(65) Prior Publication Data
US 2002/0160134 A1 Oct. 31, 2002

(51) Int. Cl.[7] ............................................. A61M 25/10
(52) U.S. Cl. ............................ 128/207.15; 604/100.01; 604/100.02; 606/192
(58) Field of Search .................. 604/100.01, 100.02, 604/100.03, 101.05; 606/192, 194; 128/207.14, 207.15

(56) References Cited

U.S. PATENT DOCUMENTS

| | | | | |
|---|---|---|---|---|
| 3,543,758 A | * | 12/1970 | McWhorter | |
| 3,543,759 A | * | 12/1970 | McWhorter | |
| 3,642,005 A | * | 2/1972 | McGinnis | |
| 4,016,885 A | * | 4/1977 | Bruner | |
| 4,018,231 A | | 4/1977 | Wallace | |
| 4,134,407 A | | 1/1979 | Elam | |
| 4,335,723 A | * | 6/1982 | Patel | |
| 4,973,305 A | * | 11/1990 | Goltzer | 604/51 |

FOREIGN PATENT DOCUMENTS

| | | |
|---|---|---|
| GB | 2 108 971 | 5/1983 |
| WO | WO 95/22367 | 8/1995 |

* cited by examiner

Primary Examiner—Michael H. Thaler
(74) Attorney, Agent, or Firm—Oblon, Spivak, McClelland, Maier & Neustadt, P.C.

(57) ABSTRACT

A balloon catheter and its pilot balloon system visually indicate the state of the inflation of a balloon placed in a human body. The small pilot balloon is conveniently manufactured by blow molding utilizing substantially the same material and has substantially the same structure as the main balloon. The pilot balloon is useful for a catheter with balloon or a tube with cuff where the balloon or the cuff is made of a very resilient material. The preferred material is a blend of composition having certain properties comprising styrenic thermoplastic elastomer and polyolefin.

12 Claims, 2 Drawing Sheets

PILOT BALLOON FOR BALLOON CATHETERS

BACKGROUND OF THE INVENTION

1. Field of the Invention

The present invention is directed to balloon catheters and systems for monitoring the inflation of balloon catheters. The invention is also directed to materials and methods used to manufacture balloon catheters.

2. Discussion of the Background

Many kinds of catheters with balloons, including urethral Foley catheters, embolectomy catheters, gastrostomy tubes, endotracheal tubes and tracheotomy tubes, are widely utilized in clinical applications. The balloons are used as inflatable retention devices or for closing ducts and passageways in the human body. These catheters have been manufactured using various materials including natural rubber, silicone rubber, polyurethane, nylon, and plasticized polyvinyl chloride. The inflation status of the main balloon (the term main balloon is sometimes used to clearly distinguish the main balloon from the pilot balloon) in the body is usually detected by the pressure sensed between two fingers at the pilot balloon which is in air tight connection with the main balloon and is located outside the human body. The thickness of the wall of the pilot balloon usually has not allowed visual indication of the inflation status of the main balloon. A pressure gauge is available to indicate the inflation pressure of the balloon of an endotracheal tube, but is not widely used in clinical situations because the pressure gauge is cumbersome and obstructs operations on the patient.

The endotracheal tube, the main tube, or the shaft and the balloon are generally made of flexible polyvinyl chloride. When an endotracheal tube is used for mechanical ventilation during anesthesia with nitrous oxide, the balloon placed in the trachea is known to gradually increase in the degree of its inflation and in its pressure because of the diffusion of nitrous oxide into the balloon caused by the difference of partial pressure across the balloon membrane. The increase in the pressure of the balloon may injure the tracheal tissue pressed by the balloon because of blockage of the blood micro-circulation in the tissue. Thus, frequent regulation of the inflation pressure is needed by using a pilot balloon.

A product, called the Brandt system, which has a large pilot balloon with a thin wall membrane to diffuse out the nitrous oxide into the air, is marketed by Mallinckrodt, but the endotracheal tube with this system is not widely used because of the difficulties in using the large pilot balloon.

Another product called the Lanz system, which was developed to automatically control the pressure of the balloon with a large pilot balloon made of a material with an early yield point at the stress-strain curve, is marketed by Mallinckrodt but is not widely used either, because of the difficulties caused by its large size. Flexible polyvinyl chloride has excellent mechanical properties for disposable medical products, but has less balloon elasticity and has problems with plasticizers and the generation of dioxines during improper incineration.

It has previously been proposed in Patel, U.S. Pat. No. 4,335,723, to make a catheter having a balloon made of thermoplastic elastomer composition comprising block copolymer (Kraton G-61650 or G-1652) in the form of end blocks of polystyrene and elastomeric center block of saturated hydrocarbon polymer, mineral oil, polypropylene and antidegradants. It is disclosed in this patent that the balloon can be made by injection molding or by blow molding a tube of the desired dimension and wall thickness, which is cut to length to provide a collar or sleeve capable of being slipped over the shaft or tube of the catheter and capable of being bonded thereto along the margins of the collar or sleeve by an appropriate adhesive. However, this patent did not disclose the composition of thermoplastic elastomer suitable for the blow molding of thin walled balloons and did not provide ways to manufacture thin walled balloons which would inflate evenly under a low pressure that is safe to the tissue of the trachea.

Inflatable cuff-type catheters were recently developed utilizing alternative materials to flexible polyvinyl chloride or thermoplastic elastomer compositions similar to that disclosed by the above patent. A thin walled balloon was successfully blow molded and bonded to a shaft. The balloon was inflated at a low pressure safe to the tissue of trachea. However, the inflation status of the balloon, invisible from the outside of the human body, was impossible to detect by the conventional pilot balloon, because the composition of the balloon was very resilient and the inflation pressure was low as long as the wall of the balloon was not unreasonably thick.

Balloon or cuff pressure indicators are known from Bruner, U.S. Pat. No. 4,016,885, and Elam, U.S. Pat. No. 4,134,407. The former patent proposed the use of an open-ended spring wound at the mid-section of the pilot balloon to allow the spring to expand to show the gas pressure or the expansion of the balloon. The latter patent proposed an elastomer pilot balloon housed in a rigid cage having a plurality of windows to indicate the state of inflation and the pressure of the internal main balloon. These patents have disclosed a pilot balloon with an inner shaft but have not considered the similarity of materials of the balloon and the pilot balloon and have not disclosed a composition to enable the blow molding of balloons.

SUMMARY OF THE INVENTION

It is an object of this invention to provide a pilot balloon assembly for a safer balloon catheter, in which the pilot balloon assembly can visually indicate the inflation status of a main balloon made of very resilient material.

According to the present invention, the above and other objects are addressed by providing a small pilot balloon which visually indicates the status of the inflation of the main balloon in the human body. The small pilot balloon inflates similarly to the main balloon. The pilot balloon is conveniently manufactured of substantially the same material and has substantially the same structure as the main balloon based on the discovery that a thin walled balloon can be manufactured by blow molding if the material has certain properties. The size of the pilot balloon, which is easily measurable with an attached scale, is proportional to the size of the balloon in the body.

This invention is useful for a catheter with a balloon or a tube with a cuff, especially as an endotracheal tube where the balloon or the cuff is manufactured from a patient friendly resilient material which includes a blend of hydrogenated styrenic thermoplastic elastomer of styrene-isoprene/butadiene-styrene block copolymer with polyethylene/polypropylene as a preferred material.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

In the detailed description which follows, specific embodiments of balloon catheters are described. It is understood, however, that the present disclosure is not limited to these embodiments. For example, it is appreciated that the methods and materials disclosed herein may be used for many types of medical devices. Other embodiments will be apparent to those skilled in the art upon reading the following description.

The common way to check the inflation status of a main balloon of a balloon catheter which is inserted into the human body has been by the pressure of a pilot balloon, which is usually detected by fingers. This method depends largely on the feeling of experienced professionals and consumes time and attention. When the balloon is made of a very resilient material, the inflation pressure is low and the detection of the pressure difference by fingers is practically impossible. This has prevented the wide use of very resilient materials for the balloons, although a balloon made of less resilient materials can hurt the human tissues which would be pressed during the intended closure of ducts and passages in the human body by the balloons. The inventors found that the state of the balloon in the body can be visually determined from the inflation of a pilot balloon if the structure, the material, and the wall thickness of the pilot balloon are properly chosen. A feature of the present invention is to provide such a pilot balloon system. Although visual indication of the inflation status is desirable for all types of balloon catheters and tubes with a cuff, endotracheal tubes would be a popular application field of the present invention as is explained in the following.

Figure 2:
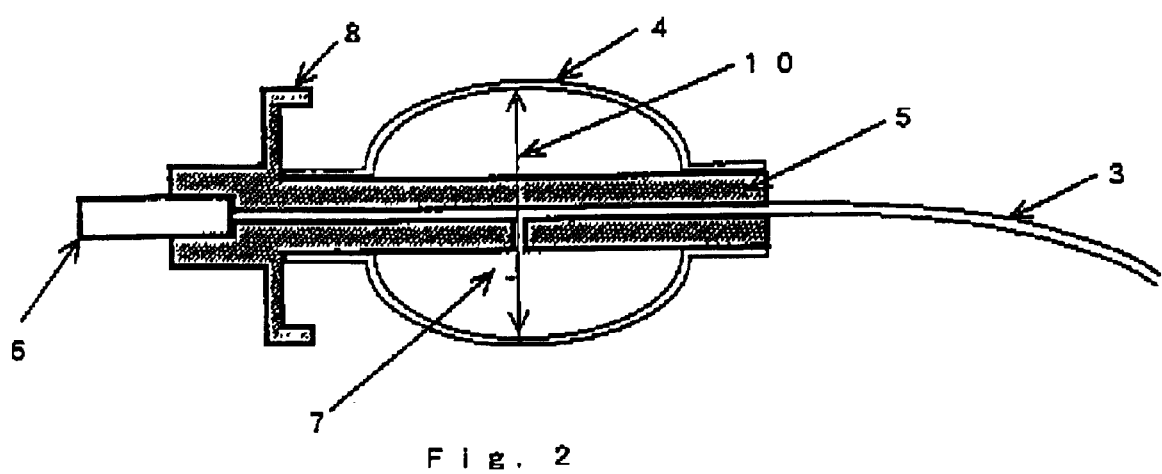
FIG. 2 is a schematic view illustrating an exemplary pilot assembly according to the present invention.

The objectives of the present invention can be met by making the inflation of the pilot balloon proportional to that of the main balloon, which can be conveniently attained by making the pilot balloon with substantially the same elastic material as the main balloon 1 and by making the structure of the pilot balloon assembly (FIG. 2) similar to that of the main balloon of the catheter. The pillar tube can be manufactured from a variety of materials, such as olefin polymers, polycarbonate, polyvinyl chloride, polystyrene, acrylonitrile butadiene, styrene copolymer, and polymethylmethacrylate. The pilot assembly should be small and light so as not to become an obstruction during clinical operations. For this reason, the diameter of the pillar is preferably between 0.2 cm and 1.0 cm and the length of the pillar is preferably between 1 cm and 3 cm.

Figure 1:
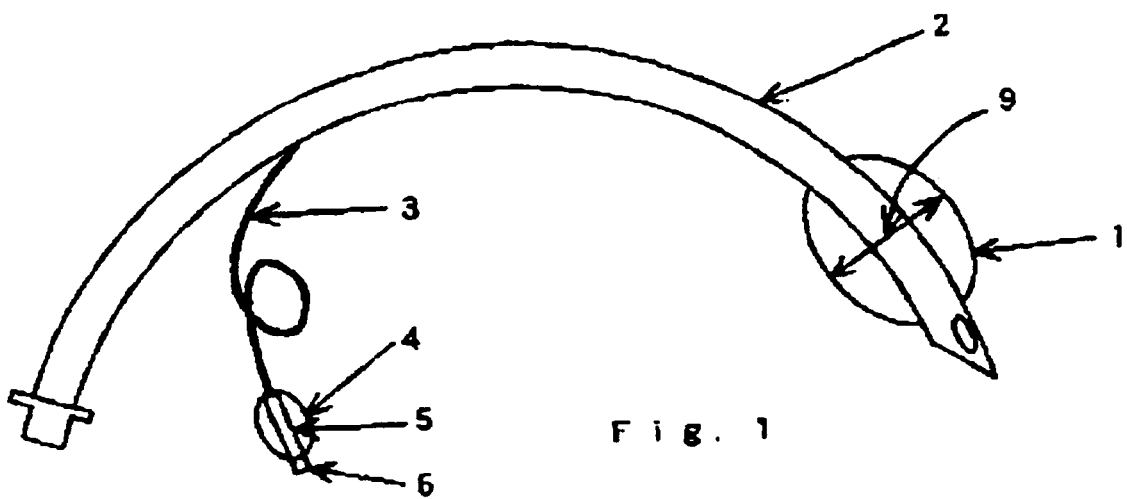
FIG. 1 is a schematic view illustrating an exemplary endotracheal tube with cuff according to the present invention.
Figure 3:
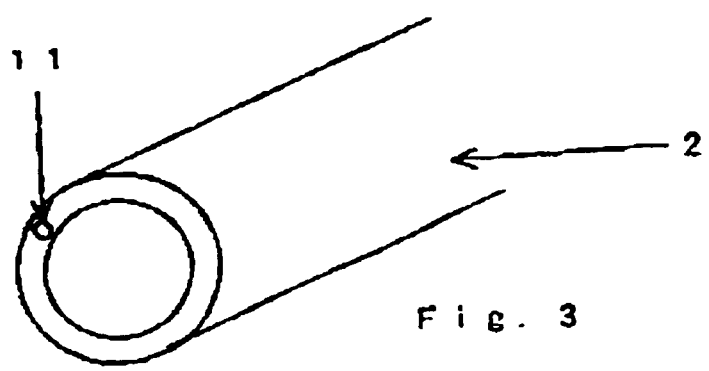
FIG. 3 is a schematic view illustrating an exemplary main tube or shaft tube according to the present invention.

The present invention is further explained using figures, for the example, of an endotracheal tube with cuff (FIG. 1). The pilot assembly (FIG. 2) is manufactured by making an air tight combination of a tube-like hollow pillar or center shaft 5, which has a hole 7 or holes, with a small pilot balloon 4. There are no special requirements for the dimensions of the holes, but a size similar to the inner diameter of the tiny tube 3 is preferable. The combination of the hollow pillar with the small balloon can be made similarly to the combination of the tube 2 with a (main) balloon 1 using a solvent or an adhesive solution, or by using melt bonding with various heating equipment. One end of the lumen of the hollow pillar or core tube 5 is connected to a one way valve 6 and the other end of the lumen of the pillar is connected to the inflation channel 11 in the main tube 2 (FIG. 3), and from there to the main balloon, through a branched tiny tube (tail tube) 3. All the connections are air tight, so that the main balloon 1 has an air tight connection with the pilot balloon 4. The diameters 9 and 10 of the balloon 1 and the pilot balloon 4 indicate the state of the inflation of the balloons, as explained in the following explanation. The pilot balloon needs to be small enough so as not to become an obstruction during clinical operations. For this reason, the diameter of the pilot balloon needs to be less than 2.0 cm at the pressure of 25 cm $H_2O$, but it also needs to be more than 0.5 cm in diameter for easy visual detection. The hollow pillar or the core tube 5 of the pilot assembly can conveniently be made a part of the outer shell of the one way valve 6.

The inflation pressure of the balloon of an endotracheal tube should be under 40 cm $H_2O$, which is the blood micro-circulation pressure at the trachea, and preferably under 30 cm $H_2O$ to prevent damage and resulting complications to the mucous tissue pressed by the balloon. It is reported for an endotracheal tube made of flexible polyvinyl chloride, the balloon pressure, initially adjusted at 20 cm $H_2O$ by air inflation, increases to 45 cm $H_2O$ in 1 hour after 66% nitrous oxide anesthesia. A lower inflation pressure would lead to the leakage of gases, so the repeated adjustment of the inflation pressure by the one way valve is desirable. However, mucous tissue damage cannot been fully prevented, because monitoring of the inflation pressure by pressing a pilot balloon is a subjective and inaccurate measurement and the repeated adjustment of the pressure is difficult in practice.

According to the present invention, the size of a pilot balloon is easily visually monitored and the critical pressure, that is, the critical size of the pilot balloon, is detected by a scale or a measure 8 located close to the pilot balloon 4. For convenience, the scale may be mounted on pillar 5. A large change of the size of a pilot balloon 4 by pressure is desirable for easy detection of the pressure. Thus, it is desirable that more than a 5% diameter change of a pilot balloon 4 be observed between a pressure change of 15 cm $H_2O$ and 40 cm $H_2O$. On the other hand, a large change in the balloon size of an endotracheal tube while in the human body by pressure is not desirable. Thus, it is desirable that the modulus and the wall thickness of the pilot balloon 4 not to be larger than that of the main balloon 1. The wall of the pilot balloon of currently available products is generally substantially thicker than that of the corresponding main balloon. If the stress-strain curve or the stress at a certain elongation and the thickness and structure of the balloon are the same as that of the pilot balloon, the degrees of inflation of the pilot balloon and the main balloon will be the same. The degree of inflation of the pilot balloon is preferably higher than that of the corresponding main balloon.

Blow molding is the most convenient way to manufacture a thin wall main balloon and a thin wall pilot balloon. The main balloon should have mechanical properties so as not to easily tear during the intubation procedure for a patient. However, if the wall of the main balloon is thick and stiff, it may hurt tissues during the intubation. Thus, a resilient and strong material is preferable for the main balloon. According to this invention, the pilot balloon is conveniently manufactured using substantially the same material as the main balloon and the wall thickness of the pilot balloon (at the thickest part) is preferably less that 0.1 mm. The thin wall of the pilot balloon needs a center shaft to support its shape. The wall thickness of a blow molded balloon is usually a minimum at the center part of the balloon and larger at the edge. Thus, the minimum wall thickness of the pilot balloon is usually at the center or at the largest diameter.

According to the present invention, an endotracheal tube comprising a main tube, a branched tiny tube, a balloon, and a pilot balloon is conveniently manufactured from compositions comprising a styrenic thermoplastic elastomer and olefin polymers, especially polyethylene or polypropylene. The composition for the balloon, the pilot balloon and the branched tiny tube can contain mineral oil. As a styrenic thermoplastic elastomer, SBS block copolymer composed of polystyrene, polybutadiene and polystyrene block, SIS block copolymer composed of polystyrene, polyisoprene and polystyrene, their hydrogenated products, their partially hydrogenated products and their blend can be used as an example, where butadiene or isoprene is polymerized in the form of 1,4, the combination of 1,4 and 1,2, the combination of 1,4 and 3,4 and the combination of 1,4,1,2, and 3, 4 bond. Isoprene and butadiene can be copolymerized. Polyethylene and polypropylene include copolymers with other modifier comonomers. The blend usually becomes more resilient when the portion of mineral oil and the styrenic thermoplastic elastomer is increased. The content of the polystyrene block in the thermoplastic elastomer should be between 10 to 40 weight %. The polystyrene block of less than 10 weight % gives poor mechanical strength to the elastomer and the polystyrene block of more than 40 weight % gives higher melt viscosity and poor mixing with polyolefin.

A preferred example of styrenic thermoplastic elastomer is SIS block copolymer where 1,2 and 3,4 bond content in the polyisoprene block is between 10 to 75 mole % and the ratio of hydrogenation of isoprene double bond is more than 70%. If the vinyl bond content (defined in this context to be 1,2 and 3,4 bond content) in polyisoprene is less then 10%, the blend with polyolefin will be turbid and if the vinyl bond content (1,2 and 3,4 bond content) in polyisoprene is more than 75%, the blend will be less elastic. If the ratio of hydrogenation is less than 70%, the compatibility of the thermoplastic elastomer with polyolefin, especially with polypropylene, becomes poor. Another preferred example of styrene thermoplastic elastomer is SBS block copolymer where 1,2 bond content in polybutadiene block is more than 45% and the ratio of hydrogenation of butadiene double bond is more than 70%. If the 1,2 bond content is less than 45%, or the ratio of hydrogenation is less than 70%, the blend with polyolefin will not be transparent. The copolymer of isoprene and butadiene can be the soft segment in the styrenic thermoplastic elastomer where vinyl content should be between 20 and 85 mole % and the degree of hydrogenation should be more than 70% for compatibility with polyolefin, especially polypropylene. The number average molecular weight of the block copolymer is preferably between 30,000 and 300,000. α-Methyl styrene and other derivatives may be used in the place of styrene to increase thermo-resistance of the block copolymer and the blend.

As olefin polymers, various polymers made of olefin monomers can be conveniently used. The examples of olefin polymers are high density polyethylene, low density polyethylene, linear low density polyethylene, high pressure ethylene-α-olefin copolymer, polypropylene, ethylene-propylene-random copolymer, block-type propylene polymer having polyethylene block and propylene-ethylene-butene-terpolymer. These olefin polymers can be used as a mixture of more than two polymers. Olefin polymers having cross-linkage by electron beam radiation or other methods can be used to increase melt tension for blow molding.

In accordance to this invention, an especially thin walled pilot balloon is conveniently blow molded from the blend having E' at 25° C. less than 350 Kgf/cm$^2$ and the melt tension MT at 230° C. higher than 1 g. If E' at 25° C. is higher than 350 Kgf/cm$^2$, the wall of a blow molded balloon becomes hard and can hurt the tissues on passing through the trachea. The composition is difficult to use to manufacture balloons by blow molding if the melt tension MT at 230° C. of the blend is less than 1 g. The storage modulus of E' at 25° C. is measured utilizing Spectro-rheometer® (Rheology Co. Japan) at 1 Hz. The melt tension of MT at 230° C. of the blend can be measured utilizing Capillograph® (Shimadzu Co. Japan) as follows. The blend preheated in the cylinder of the Capillograph at 230° C. for 4 minutes is extruded by the piston moving at the speed of 20 mm/min from the capillary of the diameter of 1 mm and the length of 10 mm. The extruded strand is pulled through the pulley at the speed of 10 m/min and the load at the pulley is recorded. The average load for 20 second after stabilization is MT at 230° C. For the blend of the MT at 230° C. lower than 1 g, a draw down of the extruded strand and a puncture of the blown up balloon is often observed in the process of blow molding. Thus the melt tension MT at 230° C. higher than 1 g is desirable for the blend comprising styrenic thermoplastic elastomer and polyolefin.

The balloons can be manufactured by blow molding the blend. The main balloon 1 and the pilot balloon 5 are bonded to the catheter of the main tube 2 and to the center hollow pillar 5 with a side hole or holes with an adhesive solution or solvent, or by a melt bond method. Well-known techniques are suitable for bonding the pilot balloon and the main balloon to their respective tubes. For a firm bond of the balloons, it is desirable to make the catheter (main tube) and the main balloon from a similar material, most conveniently from the blend of a styrenic thermoplastic elastomer and olefin polymers of different mixing ratios. The balloons would have higher proportion of styrenic thermoplastic elastomer to which oils can be added to make a more soft or resilient material.

As explained above, the present invention is especially useful for balloons made of resilient materials. The modulus of E' at 25° C. is preferably less than 350 Kgf/cm$^2$, and is more preferably less than 150 Kgf/cm$^2$ so as not to damage the tissue. The modulus of E10% and E100% which are calculated from the stress-strain curve as modulus at 10% and 100% elongation at 25° C. can better reflect the inflation status of balloons which are made of very resilient materials. The preferable E10% is smaller than 90 Kgf/cm$^2$. The present invention is useful for sheath type balloons which are fitted with center tubes without large blousing and are to inflate to a greater extent in practical uses. Thus, the more preferable E100% of the materials of the balloons is smaller than 30 Kgf/cm$^2$ for sheath type balloons.

The following examples are provided to illustrate specific examples of the blend and the inflation characteristics of a balloon made of the blend by a blow molding. These specific examples are for illustrative purpose only, and not intended to limit the scope of the invention.

EXAMPLE 1

An endotracheal tube with cuff was manufactured assembling the following parts with other common parts. A main tube of outer diameter of 11 mm and inner diameter of 8 mm was extruded using a blend comprising 70 weight % of a styrenic thermo-elastomer of hydrogenated SIS block copolymer (HYBRAR ® HVS, Kuraray, Japan; number average molecular weight about 100,000, polystyrene block content about 20 weight percent, 1.2 and 3.4 bond content in polyisoprene block 55%, and ratio of hydrogenation 90%) and a polypropylene (F327, random type polypropylene, Grand Polymer, Japan). A main balloon and a pilot balloon were blow molded using another blend comprising the same styrenic thermoplastic elastomer and a polypropylene (RD 613, block type polypropylene, Montell SKD Sunrise Ltd.)

(blend ratio: 70/30 by weight), a mineral oil (PW380, Idemitsu, Japan) composition (35% of the blend) and talc (5% of the blend). The blend showed the following properties: E'@25° C.:149 Kgf/cm², E10%:60 Kg/fcm², E100%:17 Kgf/cm², and MT at 230° C.:1.84 g. The main tube, the main balloon and the pilot balloon were assembled into a tracheal tube with cuff, such as shown in FIG. 1. The average thickness of the non-inflated main balloon at the largest diameter obtained from measurements at three different locations was 0.04 mm and the same for the pilot balloon was 0.03 mm. In a model experiment for a clinical application, air was infused through a one way valve using a syringe. The diameter of the main balloon and the pilot balloon at certain inflation air pressures were as follows: 32 mm and 18 mm at 25 cm H₂O, 33 mm and 20 mm, at 38 mm H₂O, respectively. The experiment shows that the inflation status of the main balloon is clearly shown by the pilot balloon.

EXAMPLE 2

A main balloon and a pilot balloon were blow molded using two blends of slightly different compositions comprising a styrenic thermoplastic elastomer, a polypropylene and talc. The main balloon was made of a blend of the same styrenic thermoplastic elastomer and polypropylene as used in example 1 (blend ratio; 75/25 by weight) and talc (5 weight % of the blend). The modulus of the blend were as follows: E'@25° C.:336 Kgf/cm², E10%:88 Kgf/cm², E100%:22 Kgf/cm². The melt tension of the blend MT 230° C. was 1.86 g. The pilot balloon was made of the same composition used to make the balloons in example 1. The main balloon and the pilot balloon were assembled into an endotracheal tube as shown in FIG. 1 using the main tube described in the example 1. The thickness of the wall of the main balloon and the pilot balloon measured as in the example 1 were 0.04 mm, and 0.03 mm, respectively. The diameter of the main balloon and the pilot balloon at three different inflation pressures were 31 mm and 16 mm at 25 cm H₂O, 32 mm and 17 mm at 34 cm H₂O, and 34 mm and 18 mm, at 56 cm H₂O, respectively. The inflation experiment was reproducible. Thus the diameter of a pilot balloon can indicate the inflation pressure of the balloon.

EXAMPLE 3

An endotracheal tube was prepared using a main tube described in example 1, a main balloon blow molded using the blend used in example 2 for the main balloon and a pilot balloon blow molded using the blend used in example 1. The measurements of wall thickness for the main balloon and the pilot balloon were 0.06 mm and 0.03 mm, respectively. The diameters of the main balloon and the pilot balloon at two inflation air pressures were 30 mm and 18 mm at 25 cm H₂O, 31 mm and 19 mm at 35 cm H₂O.

EXAMPLE 4

Flexible polyvinyl chloride of modulus E' at 25° C. of 166 Kgf/cm² was used to blow mold a main balloon and a pilot balloon. The minimum thickness and the maximum thickness were 0.05 mm and 0.26 mm for the balloon and 0.05 mm and 0.15 mm for the pilot balloon. The balloon and the pilot balloon were assembled into an endotracheal tube as is show in FIG. 1 with a flexible polyvinyl chloride main tube of outer diameter 11 mm. The diameters of the balloon and the pilot balloon at an air pressure of 25 cm H₂O were 35 mm and 15 mm, respectively. The change of the diameter at increasing the inflation pressure up to 50 cm H₂O was not remarkable. However, the pilot balloon indicated, at least, that the balloon was at the state of inflation.

Numerous modifications and variations of the present invention are possible in light of the above teachings. For example, features described for certain embodiments may be combined with other embodiments described herein. It is therefore to be understood that within the scope of the appended claims, the invention may be practiced otherwise than as specifically described herein.

What is claimed as new and desired to be secured by Letters Patent of the United States is:

1. A balloon catheter comprising:
   a main balloon;
   a pilot balloon having an elasticity substantially identical to that of the main balloon; and
   an air tube fluidly connected to the main balloon and the pilot balloon and supporting the main balloon and the pilot balloon,
   wherein an inflation state of the pilot balloon is substantially proportional to an inflation state of the main balloon,
   wherein the main balloon and the pilot balloon are formed of a blow molded blend comprising a styrenic thermoplastic elastomer and polyolefins, the styrenic thermoplastic elastomer has polystyrene block of weight % between 10% and 40% the styrenic thermoplastic elastomer has hydrogenated soft segment block of at least one of the group comprising polyisoprene, copolymer of isoprene and butadiene, and polybutadiene, a vinyl bond content (1,2 and 3,4 bond content) of polyisoprene is between 10 to 75 mole %, a vinyl bond content (1,2 and 3,4 bond content) of the copolymer of isoprene and butadiene is between 20 and 85 mole %, a vinyl bond content (1,2 bond content) in polybutadiene block is more than 45 mole %, and a degree of hydrogenation is more than 70%.

2. The balloon catheter according to claim 1, further comprising an inflation scale attached to the air tube.

3. The balloon catheter according to claim 1, wherein the pilot balloon is smaller than the main balloon and comprises a substantially same material as the main balloon.

4. The balloon catheter according to claim 1, wherein the pilot balloon has a minimum wall thickness of less than 0.1 mm.

5. The balloon catheter according to claim 2, wherein the inflation scale is adjacent to the pilot balloon.

6. The balloon catheter according to claim 1, wherein a diameter of the said pilot balloon at an inflation pressure of 25 cm H₂O is less than 2.0 cm and more than 0.5 cm.

7. The balloon catheter according to claim 1, wherein both the main balloon and the pilot balloon start to inflate at a pressure of less than 15 cm H₂O, and a diameter of the pilot balloon increases more than 5% when the pressure of the main balloon and the pilot balloon increases from 15 cm H₂O to 40 cm H₂O.

8. The balloon catheter according to claim 1, wherein the blend has the properties of E' at 25° C. at 1 Hz lower than 350 Kgf/cm² and melt tension at 230° C. higher than 1 g.

9. The balloon catheter according to claim 1, wherein the blend of the pilot balloon comprises a mineral.

10. The balloon catheter according to claim 9, wherein the balloon catheter is an endotracheal tube.

11. The balloon catheter according to claim 1, wherein the pilot balloon comprises a substantially same material as the main balloon.

12. The balloon catheter according to claim 1, wherein the average thickness of the non-inflated main balloon at the largest diameter is 0.04 mm and the average thickness of the non-inflated pilot balloon at the largest diameter is 0.03 mm.

* * * * *